(12) United States Patent
Li et al.

(10) Patent No.: US 11,955,245 B2
(45) Date of Patent: Apr. 9, 2024

(54) METHOD AND SYSTEM FOR MENTAL INDEX PREDICTION

(71) Applicants: Acer Incorporated, New Taipei (TW); National Yang Ming Chiao Tung University, Hsinchu (TW)

(72) Inventors: Chun-Hsien Li, New Taipei (TW); Szu-Chieh Wang, New Taipei (TW); Andy Ho, New Taipei (TW); Liang-Kung Chen, Hsinchu (TW); Jun-Hong Chen, New Taipei (TW); Li-Ning Peng, Hsinchu (TW); Tsung-Han Yang, New Taipei (TW); Yun-Hsuan Chan, New Taipei (TW); Tsung-Hsien Tsai, New Taipei (TW)

(73) Assignees: Acer Incorporated, New Taipei (TW); National Yang Ming Chiao Tung University, Hsinchu (TW)

( * ) Notice: Subject to any disclaimer, the term of this patent is extended or adjusted under 35 U.S.C. 154(b) by 509 days.

(21) Appl. No.: 17/366,041

(22) Filed: Jul. 2, 2021

(65) Prior Publication Data
US 2022/0208383 A1    Jun. 30, 2022

(30) Foreign Application Priority Data
Dec. 31, 2020    (TW) ................................ 109147021

(51) Int. Cl.
    *G16H 30/00*      (2018.01)
    *G06T 7/00*      (2017.01)
    (Continued)

(52) U.S. Cl.
    CPC ........... *G16H 50/30* (2018.01); *G06T 7/0012* (2013.01); *G06T 7/246* (2017.01); *G16H 20/70* (2018.01);
    (Continued)

(58) Field of Classification Search
CPC ........ G16H 50/30; G16H 30/00; G16H 20/70; G06T 7/246; G06T 7/0012; G06T 2207/30201
See application file for complete search history.

(56) References Cited

U.S. PATENT DOCUMENTS

| 7,754,959 B2 * | 7/2010 | Herberger ............ G11B 27/031 84/622 |
| 10,191,920 B1 * | 1/2019 | Grundmann ........... G06V 10/95 |
| | | (Continued) |

FOREIGN PATENT DOCUMENTS

| CN | 103488293 | 1/2014 |
| CN | 106650621 | 5/2017 |
| | (Continued) | |

OTHER PUBLICATIONS

"Search Report of Europe Counterpart Application", dated Feb. 1, 2022, p. 1-p. 10.

*Primary Examiner* — Dominic E Rego
(74) *Attorney, Agent, or Firm* — JCIPRNET

(57) ABSTRACT

A method and a system for mental index prediction are provided. The method includes the following steps. A plurality of images of a subject person are obtained. A plurality of emotion tags of the subject person in the images are analyzed. A plurality of integrated emotion tags in a plurality of predetermined time periods are calculated according to the emotion tags respectively corresponding to the images. A plurality of preferred features are determined according to the integrated emotion tags. A mental index prediction model is established according to the preferred features to predict a mental index according to the emotional index prediction model.

20 Claims, 4 Drawing Sheets

(51) Int. Cl.
*G06T 7/246* (2017.01)
*G16H 20/70* (2018.01)
*G16H 30/40* (2018.01)
*G16H 50/30* (2018.01)

(52) U.S. Cl.
CPC ... *G16H 30/00* (2018.01); *G06T 2207/30201* (2013.01)

(56) References Cited

U.S. PATENT DOCUMENTS

| | | | |
|---|---|---|---|
| 10,242,034 B1* | 3/2019 | Li | G06F 16/4393 |
| 10,467,290 B1* | 11/2019 | Wu | G06F 16/9024 |
| 2014/0007149 A1* | 1/2014 | Huang | G06Q 30/0255 |
| | | | 725/12 |
| 2016/0287117 A1* | 10/2016 | Breakspear | G16H 50/20 |
| 2019/0090020 A1* | 3/2019 | Srivastava | G11B 27/28 |
| 2019/0175090 A1* | 6/2019 | Reiner | A61B 5/165 |
| 2019/0266999 A1* | 8/2019 | Chandrasekaran | G10L 15/16 |
| 2020/0130674 A1* | 4/2020 | Youn | G06F 3/013 |
| 2020/0138356 A1 | 5/2020 | Sharon et al. | |
| 2021/0097142 A1* | 4/2021 | Breedvelt-Schouten | |
| | | | H04L 12/1822 |
| 2022/0086337 A1* | 3/2022 | Subramanian | G06N 7/01 |

FOREIGN PATENT DOCUMENTS

| | | |
|---|---|---|
| CN | 109190487 | 1/2019 |
| CN | 109583431 | 4/2019 |
| CN | 109816141 | 5/2019 |
| TW | 201813584 | 4/2018 |
| TW | M579360 | 6/2019 |
| WO | 2019033573 | 2/2019 |

* cited by examiner

METHOD AND SYSTEM FOR MENTAL INDEX PREDICTION

CROSS-REFERENCE TO RELATED APPLICATION

This application claims the priority benefit of Taiwanese application no. 109147021, filed on Dec. 31, 2020. The entirety of the above-mentioned patent application is hereby incorporated by reference herein and made a part of this specification.

BACKGROUND

Technical Field

The disclosure relates to a method for emotion prediction; particularly, the disclosure relates to a method and a system for mental index prediction based on captured images.

Description of Related Art

In recent years, due to improvement in life quality, rapid development of medical technology, declining birthrate, and the like, the number of senior citizens in Taiwan has increased rapidly, and the proportion thereof in the total population has also increased each year. Therefore, the psychiatric or psychological health of elder people is one of the issues of concern in modern society. At present, evaluation on the mental condition of the elder people still mostly relies on medical personnel to perform regular evaluation, which may be accompanied with various quantifiable evaluation scales. For example, commonly seen scales include the BEHAVE-AD scale, the Cohen-Mansfield agitation inventory (CMAI), and the neuropsychiatric inventory (NPI). These scales may include up to 50% of evaluation factors related to emotions. However, for many elder people, unwillingness to express, unawareness of their own abnormal emotional changes, or forgetting the actual emotions in the past, in addition to deterioration of physical functions, may gradually lead to depression, dementia, and cognitive dysfunctions among other illnesses.

Therefore, through continuously observing the emotions of the elder people and detecting their daily emotional changes in advance through technology, prompt management, such as psychological counseling, drug treatment, etc., is possible for delaying the symptoms of various psychiatric illnesses, and improving the daily life of the elder people so as to facilitate better life quality.

SUMMARY

The disclosure proposes a method and a system for mental index prediction, in which a mental index of a subject person is predicted by continuously observing emotional expression of the subject person, thereby facilitating determination whether the subject person is with a psychiatric illness.

An embodiment of the disclosure provides a method for mental index prediction, which is adapted for a system for mental index prediction including a processor. The method includes the following steps. A plurality of images of a subject person are obtained. A plurality of emotion tags of the subject person in the images are analyzed. A plurality of integrated emotion tags in a plurality of predetermined time periods are calculated according to the emotion tags respectively corresponding to the images. A plurality of preferred features are determined according to the integrated emotion tags. A mental index prediction model is established according to the preferred features to predict a mental index according to the emotional index prediction model.

An embodiment of the disclosure provides a system for mental index prediction, which includes a storage device and a processor. The storage device records a plurality of commands. The processor is coupled to the storage device and is configured to execute the commands to: obtain a plurality of images of a subject person; analyze a plurality of emotion tags of the subject person in the images; calculate a plurality of integrated emotion tags in a plurality of predetermined time periods according to the emotion tags respectively corresponding to the images; determine a plurality of preferred features according to the integrated emotion tags; and establish a mental index prediction model according to the preferred features to predict a mental index according to the mental index prediction model.

Based on the foregoing, in the embodiment of the disclosure, an image capturing equipment may be disposed within an activity range of the subject person to continuously obtain facial expression information of the subject person. The emotion tags of the subject person in the images is generated based on the facial expression information of the subject person, and the integrated emotion tags belonging to the predetermined time periods are obtained. Based on this, after the preferred features that are highly correlated with a predicted result is extracted based on the integrated emotion tags, an accurate mental index prediction model is established according to the preferred features to predict the mental index according to the mental index prediction model. Therefore, in the embodiment of the disclosure, the predicted mental index is generated according to long-term continuous observation of the subject person, which is of considerable reliability, facilitating diagnosis of psychiatric illnesses.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
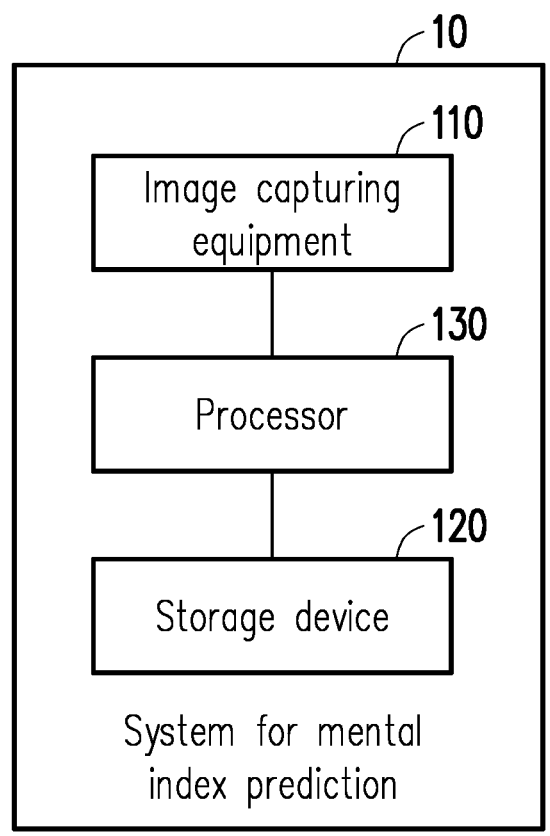
FIG. 1 is a functional block diagram of a system for mental index prediction according to an embodiment of the disclosure.

FIG. 1 is a functional block diagram of a system for mental index prediction according to an embodiment of the disclosure. However, this is only for the convenience of explanation, and is not used to limit the disclosure. First, FIG. 1 introduces all components and relationships of configuration of the system for mental index prediction.

Detailed functions thereof will be disclosed in conjunction with the following embodiments.

With reference to FIG. 1, a system for mental index prediction 10 includes image capturing equipment 110, a storage device 120, and a processor 130. The processor 130 is coupled to the image capturing equipment 110 and the storage device 120. In some embodiments, the system for mental index prediction 10 may include a computer device that includes the storage device 120 and the processor 130, and the image capturing equipment 110 connected to the computer device. For example, the system for mental index prediction 10 may be composed of a computer and an external camera, but is not limited thereto. Alternatively, in some embodiments, the system for mental index prediction 10 may further include a communication interface, which transmits the image data captured by the image capturing equipment 110 through a network (e.g., the Internet) to a computer device, such as a server, that includes the storage device 120 and the processor 130.

The image capturing equipment 110 is configured to capture images of a subject person, and includes a camera lens that includes a lens element and a photosensitive element. The photosensitive element is configured to sense the intensity of light entering the lens element to generate an image. The photosensitive element may be, for example but not limited to, a charge coupled device (CCD), a complementary metal-oxide semiconductor (CMOS) element, or other elements.

The storage device 120 is configured to store files, images, commands, program codes, software elements, and other data, which may be, for example, a fixed or mobile device in any form, such as a random access memory (RAM), a read-only memory (ROM), a flash memory, a hard disk, or the like, an integrated circuit, and a combination thereof.

The processor 130 is configured to execute the proposed method for mental index prediction, which is, for example, a central processing unit (CPU), or any other programmable general-purpose or special-purpose microprocessor, a digital signal processor (DSP), a programmable controller, an application specific integrated circuit (ASIC), a programmable logic device (PLD), a graphics processing unit (GPU), or the like or a combination of these devices. The processor 130 may execute the program codes, software modules, commands, etc. recorded in the storage device 120 to realize the method for mental index prediction of the embodiment of the disclosure.

Figure 2:
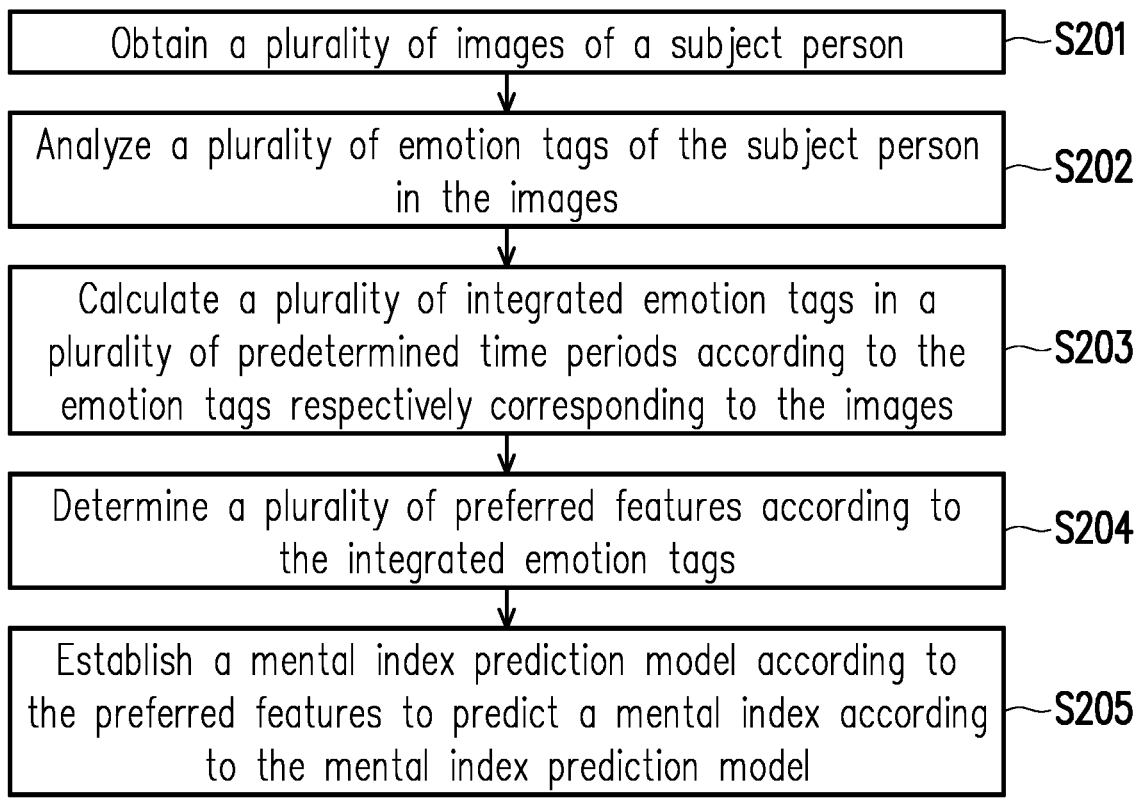
FIG. 2 is a flowchart of a method for mental index prediction according to an embodiment of the disclosure.

FIG. 2 is a flowchart of a method for mental index prediction according to an embodiment of the disclosure. With reference to FIG. 2, the method in this embodiment is adapted for the system for mental index prediction 10 in the above embodiment. Hereinafter, detailed steps of the method in this embodiment will be described accompanied with the elements in the system for mental index prediction 10.

In step S201, the processor 130 obtains a plurality of images of a subject person from the image capturing equipment 110. In some embodiments, the image capturing equipment 110 may be disposed within a daily activity range of the subject person to capture the images of the subject person.

In step S202, the processor 130 analyzes a plurality of emotion tags of the subject person in the images. In some embodiments, the processor 130 may detect a plurality of facial image blocks of the subject person in the images using facial detection technology. For example, the processor 130 may locate a facial image block of the subject person in each of the images using a facial detection model. In addition, the processor 130 may detect a plurality of facial landmarks for tagging a facial contour, shapes of the five sense organs, and positions of the five sense organs from the facial image block using machine learning, deep learning, or other suitable algorithms. In some embodiments, the processor 130 may filter the images based on a size of the facial image block and a deflection angle of the face, so as to retain images with a sufficiently large facial image block and a sufficiently small deflection angle of the face. Based on this, images with insufficient facial information may be eliminated to prevent establishing a mental index prediction model with training data of low reliability. Besides, in some embodiments, the processor 130 may also verify an identity of the subject person according to the facial image block in the image to avoid access to facial information of other people.

Next, in some embodiments, the processor 130 may input the facial image blocks into a facial expression categorization model to obtain the emotion tags respectively corresponding to the images. This facial expression categorization model may be a categorizer that has been trained in advance through machine learning, which categorizes and tags facial emotions of the subject person in each of the images. For example, the processor 130 may categorize the facial emotions in the facial image blocks into a plurality of emotion categories using the facial expression categorization model, and obtain the emotion tags respectively corresponding to each of the images according to a categorization result. In some embodiments, the emotion tags may be discrete values, such as 1, 2, 3, 4, and so on, and these values are positively correlated with positivity of the emotion. That is to say, as the value of the emotion tag increases, the emotion of the subject person is increasing positive, and as the value of the emotion tag decreases, the emotion of the subject person is increasingly negative. However, the disclosure does not limit the categorization number and actual value of the emotion tags, and they may be designed depending on actual needs.

In step S203, the processor 130 calculates a plurality of integrated emotion tags in a plurality of predetermined time periods according to the emotion tags respectively corresponding to the images. In some embodiments, the processor 130 performs a statistical calculation on the emotion tags in each of the predetermined time periods and obtains one of the integrated emotion tags in each of the predetermined time periods. The statistical calculation is, for example, an averaging operation or a mode obtaining process, etc. Specifically, a duration of the predetermined time period uses, for example, "one day" as a unit, and these predetermined time periods are thus a plurality of dates, but the disclosure is not limited thereto. The image capturing equipment 110 may capture the images of the subject person on each day, and the processor 130 may obtain the emotion tags of each day according to the images of the subject person. In addition, the processor 130 may integrate all the emotion tags of each day and obtain the integrated emotion tags respectively corresponding to different days. For example, Table 1 shows emotion tags of a certain subject person, and Table 2 shows integrated emotion tags of this subject person. Herein, it is assumed that the emotion tags include 4 categories, respectively '1', '2', '3', and '4'.

TABLE 1

| Subject person no. | Date | Emotion tag |
| --- | --- | --- |
| A | Mar. 6, 2019 | 3 |
| A | Mar. 6, 2019 | 4 |
| A | Mar. 6, 2019 | 3 |
| A | Mar. 7, 2019 | 1 |
| A | Mar. 7, 2019 | 1 |
| ... | ... | ... |

TABLE 2

| Subject person no. | Date | Integrated emotion tag |
| --- | --- | --- |
| A | Mar. 6, 2019 | 3 ({0, 0, 2, 1}) |
| A | Mar. 7, 2019 | 1 ({2, 0, 0, 0}) |
| ... | ... | ... |

Notably, in some embodiments, the mental index prediction model may predict an NPI score according to a daily emotional expression of the subject person. In other words, the real information configured to train the mental index prediction model is the NPI score generated as the subject person actually answers the NPI questionnaire. Therefore, the processor 130 may integrate N integrated emotion tags from N days before the day on which an NPI test is actually performed, and take the N integrated emotion tags as a training data set for training the mental index prediction model. For example, Table 3 is a training data set for training a mental index prediction model regarding a certain subject person.

TABLE 3

| Subject person no. | NPI test date | Integrated emotion tag 1 day before | Integrated emotion tag 2 days before | Integrated emotion tag 3 days before | ... | Integrated emotion tag N days before |
| --- | --- | --- | --- | --- | --- | --- |
| A | Mar. 9, 2019 | 2 | 1 | 3 | ... | 2 |
| A | June 12, 2019 | 2 | 1 | 1 | ... | 1 |
| ... | ... | ... | ... | ... | ... | ... |

In step S204, the processor 130 determines a plurality of preferred features according to the integrated emotion tags. In some embodiments, the processor 130 may generate a plurality of initial features according to a plurality of predefined feature generation rules and the integrated emotion tags. In some embodiments, the processor 130 may obtain a part or all of the initial features according to the integrated emotion tags. In some embodiments, the initial features may include the integrated emotion tags and their statistical calculation results. In some embodiments, the processor 130 may directly take the initial features as the preferred features. In some embodiments, the processor 130 may perform feature extraction on the initial features to extract relatively important preferred features, and these preferred features correspond to a part of the predefined feature generation rules. That is to say, in some embodiments, the preferred features may include the integrated emotion tags. In some embodiments, the preferred features may include the statistical calculation results of the integrated emotion tags. In some embodiments, the preferred features may include the integrated emotion tags and their statistical calculation results. The statistical calculation results of the integrated emotion tags may include an average, a standard deviation, and other statistical information. Detailed description will be provided in the following embodiments. Incidentally, in other embodiments, the initial features that may be selected as the preferred features may also include a sleep quality index and an activity level index of the subject person that are estimated according to the images. Detailed description will be provided in the following embodiments.

In step S205, the processor 130 establishes a mental index prediction model according to the preferred features to predict the mental index according to the mental index prediction model. In some embodiments, according to a real mental index (e.g., an NPI score obtained from an actual NPI test) and the selected preferred features serving as training data of a supervised machine learning algorithm, the processor 130 may establish the mental index prediction model. That is to say, the processor 130 may establish the mental index prediction model according to a machine learning algorithm and training data. The above-mentioned machine learning algorithm may include, for example but not limited to, a regression analysis algorithm, multivariate adaptive regression splines (MARS) algorithm, bootstrap aggregating (bagging) algorithm, neural network algorithm, random forest algorithm, elastic net algorithm, least absolute shrinkage and selection operator (LASSO) algorithm, k-nearest neighbor classification (KNN) algorithm, support-vector regression (SVR) algorithm, or the like.

To be specific, during a training phase of the mental index prediction model, the processor 130 tags the data set formed of a plurality of integrated mental indexes based on the real NPI score, and takes the preferred features of the tagged data set as training materials for machine learning. Taking Table 3 as an example, the processor 130 tags a data set including N integrated mental indexes from N days before the test date according to a NPI score obtained from an NPI test performed on Mar. 9, 2019, and takes the preferred features established with the N integrated mental indexes as the training materials for machine learning. Based on this, in some embodiments, the processor 130 may train the mental index prediction model adapted for predicting the mental index according to the data for one or more subject persons. Thereby, this mental index prediction model predicts the mental index of the subject person according to the continuous daily emotional expression of the subject person, facilitating diagnosis of psychiatric illnesses. However, although prediction with the NPI score is taken as an example for explanation in the foregoing embodiment, in other embodiments, the mental index may be an index value generated based on other scales or tests.

Figure 3:
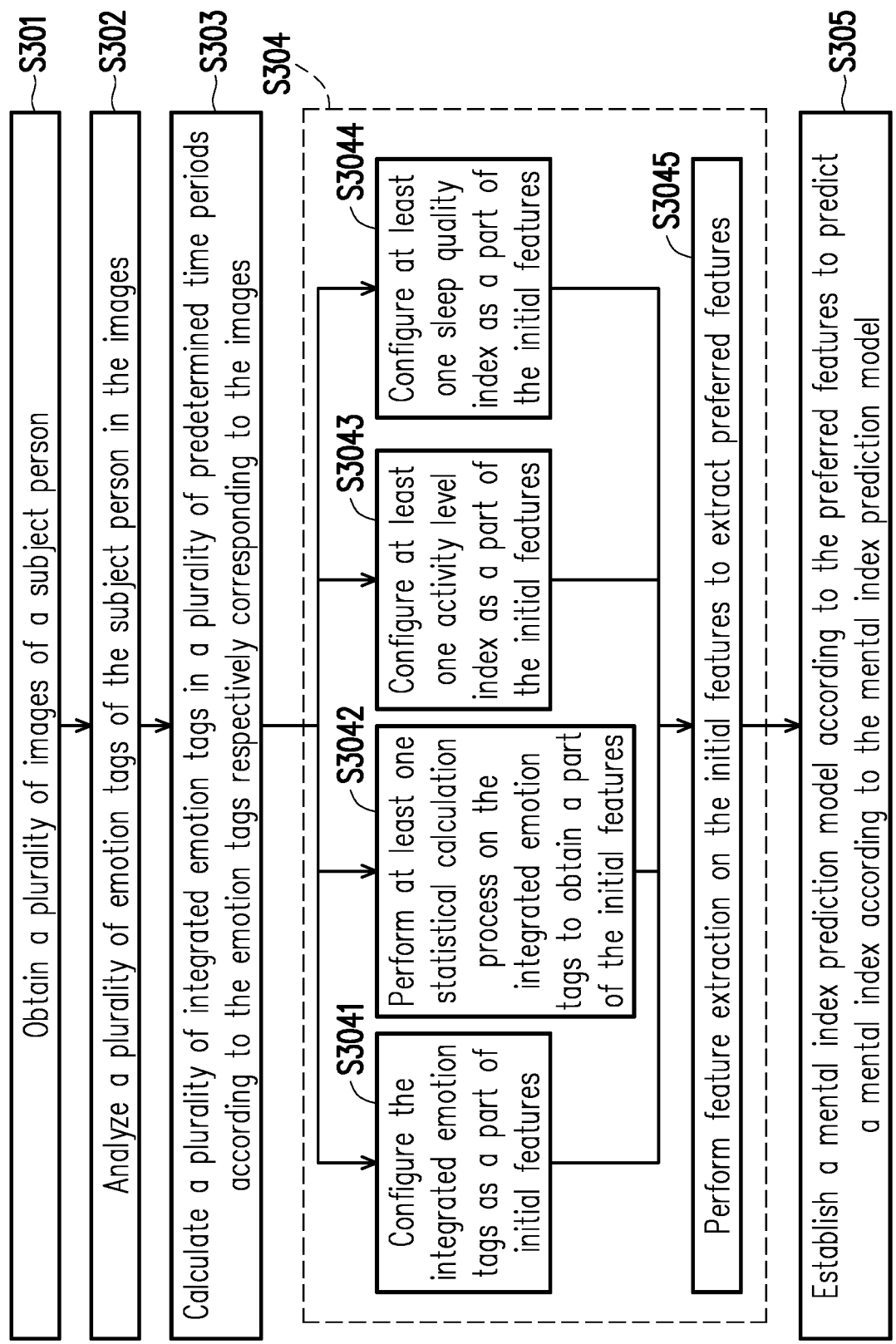
FIG. 3 is a flowchart of a method for mental index prediction according to an embodiment of the disclosure.

FIG. 3 is a flowchart of a method for mental index prediction according to an embodiment of the disclosure. With reference to FIG. 3, the method in this embodiment is adapted for the system for mental index prediction 10 in the foregoing embodiment. Hereinafter, detailed steps of the method in this embodiment will be described accompanied with the elements in the system for mental index prediction 10.

In step S301, the processor 130 obtains a plurality of images of a subject person from the image capturing equipment 110. In step S302, the processor 130 analyzes a plurality of emotion tags of the subject person in the images. In step S303, the processor 130 calculates a plurality of integrated emotion tags in a plurality of predetermined time periods according to the emotion tags respectively corresponding to the images. The operations of steps S301 to S303 described above are similar to those of steps S201 to S203 as shown in FIG. 2.

In step S304, the processor 130 determines a plurality of preferred features according to the integrated emotion tags. In this embodiment, step S304 may be implemented as step S3041 to step S3045. In this embodiment, the processor 130 may first establish a plurality of initial features, and then perform feature extraction on the initial features to select the preferred features. In this embodiment, the initial features may include the integrated emotion tags, statistical calculation results of the integrated emotion tags, a sleep quality index of the subject person, and an activity level index of the subject person.

Therefore, in step S3041, the processor 130 configures the integrated emotion tags as a part of the initial features. For example, the processor 130 may directly configure 7 integrated emotion tags from 7 days before the NPI test date as 7 initial features.

In step S3042, the processor 130 performs at least one statistical calculation process on the integrated emotion tag to obtain a part of the initial features. Assuming that the 7 integrated emotion tags from the 7 days before the NPI test are respectively E1, E2, E3, E4, E5, E6, and E7. For the convenience of description hereinafter, it is taken as an example that the integrated emotion tags are categorized into 4 categories of emotions, respectively '1', '2', '3', and '4'. In some embodiments, the processor 130 may calculate a mean value Mn of the integrated emotion tags E1 to E7 to obtain an initial feature. In some embodiments, the processor 130 may count frequencies of occurrences C1 to C4 of the 4 emotions '1', '2', '3', and '4' according to the integrated emotion tags E1 to E7 to obtain 4 initial features. In some embodiments, the processor 130 may calculate a standard deviation SD of the integrated emotion tags E1 to E7 to obtain an initial feature.

In some embodiments, it is assumed that the emotions '1' and '2' are positive emotions, and the emotions '3' and '4' are negative emotions. The processor 130 may calculate a sum Pos of the frequencies of occurrences C1 and C2 of the positive emotions '1' and '2' to obtain an initial feature. Also, the processor 130 may calculate a sum Neg of the frequencies of occurrences C3 and C4 of the negative emotions '3' and '4' to obtain an initial feature. In some embodiments, the processor 130 may even calculate a difference Diff between the sum Pos of the positive emotions and the sum Neg of the negative emotions to obtain an initial feature. Besides, in some embodiments, the processor 130 also establishes an initial feature according to an emotional change between two adjacent days. For example, in some embodiments, the processor 130 may calculate a sum Diff sum of the differences between the integrated emotion tags of two adjacent days and obtain an initial feature, where the initial feature may be represented as |E1−E2|+|E2−E3|+|E3−E4|+|E4−E5|+|E5−E6|+|E6−E7|. In some embodiments, the processor 130 may calculate a range Range of the differences between the integrated emotion tags of two adjacent days to obtain an initial feature, where this initial feature may be represented as Max(|E1−E2|, |E2−E3|, |E3−E4|, |E4−E5|, |E5−E6|, |E6−E7|)−Min(|E1−E2|, |E2−E3|, |E3−E4|, |E4−E5|, |E5−E6|, |E6−E7|).

For example, assuming that E1, E2, E3, E4, E5, E6, and E7 are respectively 1, 2, 2, 3, 2, 4, and 1, then the processor 130 obtains a plurality of initial features as shown in Table 4 according to a plurality of statistical calculations.

TABLE 4

| Subject person no. | Mn | C1 | C2 | C3 | C4 | SD |
|---|---|---|---|---|---|---|
| A | 2.14 | 2 | 3 | 1 | 1 | 1.07 |
| Subject person no. | Pos | Neg | Diff | Diff_sum | Range | |
| A | 5 | 2 | 3 | 8 | 3 | |

In step S3043, the processor 130 obtains at least one activity level index of the subject person according to the images, and configures the at least one activity level index as a part of the initial features. In some embodiments, obtaining the images from the subject person is not limited to obtaining emotion-related features, but may as well include estimating an activity level of the subject person in the images, such as a movement distance, an amount of limb and skeleton changes, a magnitude of change of walking trajectories across multiple images in a single day, and the like, according to the images. Taking the movement distance as an example, the processor 130 may determine whether the subject person in the image is standing or not and whether the subject person is walking, to thereby calculate a cumulative walking time. The movement distance may be a product of the walking time and an average walking velocity of the subject person. The average walking velocity of the subject person may be set depending on the age and the gender. In other words, in some embodiments, the activity level index may include the movement distance of the subject person, the amount of skeleton change, the magnitude of change of walking trajectories, or the like. The activity level index may be obtained from estimates using one day or multiple days as a unit. In some embodiments, the processor 130 may also perform statistical calculations on the activity level indexes of different days to obtain other initial features.

In step S3044, the processor 130 obtains at least one sleep quality index of the subject person according to the images or another instrument, and configures the at least one sleep quality index as a part of the initial features. In some embodiments, a sleep quality of the subject person, such as a sleep duration of a single day, a proportion of deep/light sleep to the sleep duration, the times of getting out of bed/turning over, etc., may be detected through a smart instrument, such as a smart mattress or a wearable electronic device. The sleep quality index may be obtained from estimates using one day or multiple days as a unit. In some embodiments, the processor 130 may also perform statistical calculations on the sleep quality indexes of different days to obtain other initial features.

In step S3045, the processor 130 performs feature extraction on the initial features to extract the preferred features. Specifically, the processor 130 trains the corresponding prediction model according to all of the initial features and various machine learning algorithms, and further sorts each of the initial features according to a feature weight, a feature importance, or a feature relevance of each of the initial features to select some of the features that are top-ranked. For example, corresponding to different machine learning algorithms, the processor 130 may sort each of the initial features according to a P-value, an Akaike information criterion (AIC) measurement, or the feature importance of each of the initial features. According to the frequencies or the ratio of selecting each of initial features, the processor 130 may select L preferred features from K initial features, where L≤K.

In step S305, the processor 130 establishes a mental index prediction model according to the preferred features to predict the mental index according to the mental index prediction model. The operation of step S305 is similar to that of step S205 as shown in FIG. 2, and will not be repeatedly described herein. Thereby, different from the conventional determination whether the subject person is with a psychiatric illness, such as depression or dementia, simply using a specific scale, in the embodiment of the disclosure, the future mental index may be predicted according to the change in the emotional expression, the activity level, and the sleep quality of each day, effectively facilitating diagnosis accuracy of psychiatric illnesses.

Figure 4:
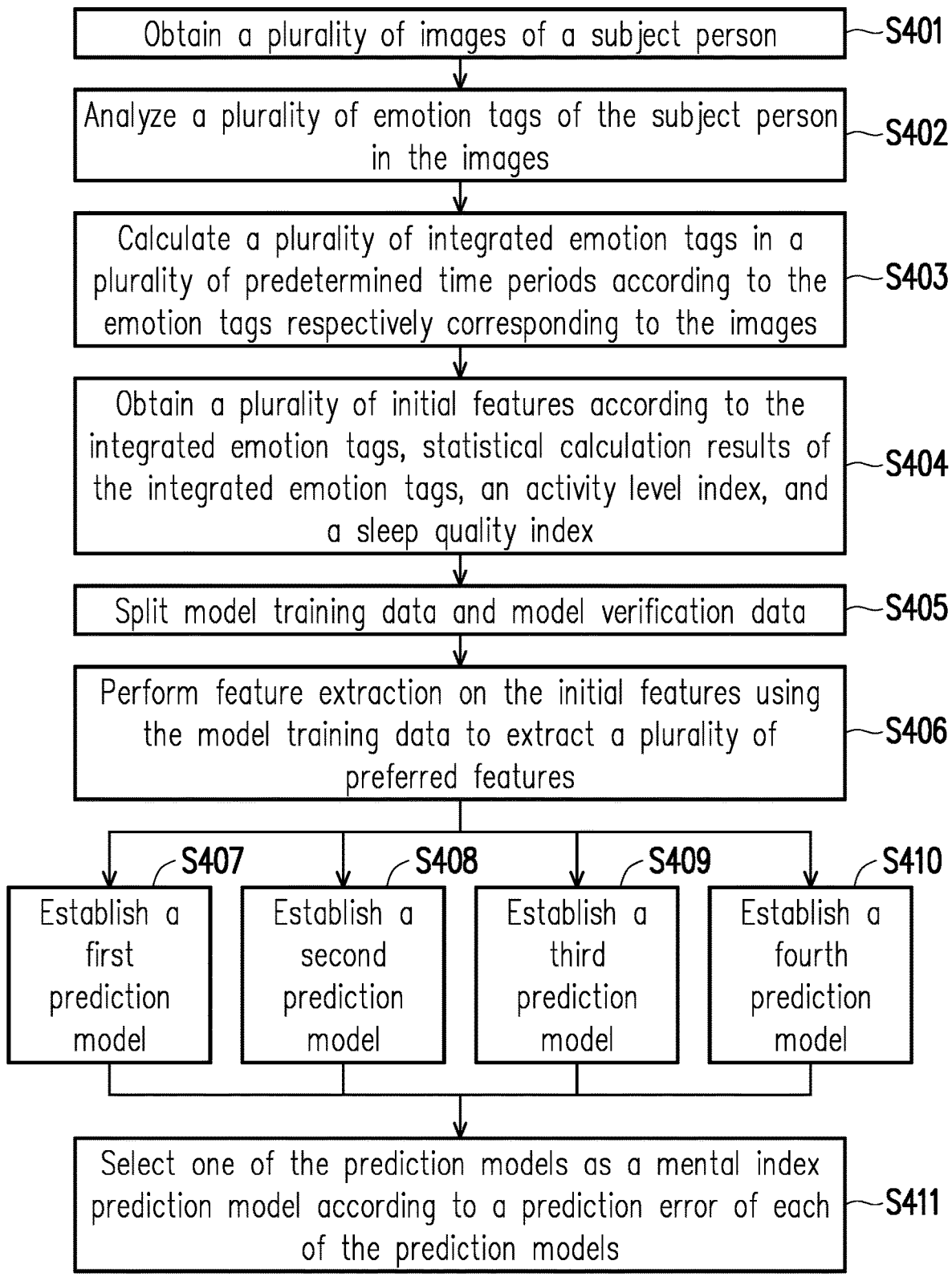
FIG. 4 is a flowchart of establishing a mental index prediction model according to an embodiment of the disclosure.

FIG. 4 is a flowchart of establishing a mental index prediction model according to an embodiment of the disclosure. With reference to FIG. 4, the method in this embodiment is adapted for the system for mental index prediction 10 in the foregoing embodiment. Hereinafter, detailed steps of the method in this embodiment will be described accompanied with the elements in the system for mental index prediction 10.

In step S401, the processor 130 obtains a plurality of images of a subject person from the image capturing equipment 110. In step S402, the processor 130 analyzes a plurality of emotion tags of the subject person in the images. In step S403, the processor 130 calculates a plurality of integrated emotion tags in a plurality of predetermined time periods according to the emotion tags respectively corresponding to the images. In step S404, the processor 130 obtains a plurality of initial features according to the integrated emotion tags, statistical calculation results of the integrated emotion tags, an activity level index, and a sleep quality index. The operations of steps S401 to S404 have been clearly described in the foregoing embodiments of FIG. 2 and FIG. 3, and will not be repeatedly described herein.

In step S405, the processor 130 splits model training data and model verification data. Splitting the model training data and the model verification data without repetition may include, for example, K-fold algorithm, and repeatable splitting the model training data and the model verification data may include, for example, bootstrap algorithm, but the disclosure is not limited thereto. In step S406, the processor 130 performs feature extraction on the initial features using the model training data to extract a plurality of preferred features. As explained in the embodiment of FIG. 3, the processor 130 may perform feature extraction on the initial features based on a variety of different machine learning algorithms to select preferred features that are more related to outputs of the model from the initial features.

Notably, in some embodiments, the processor 130 may establish a plurality of prediction models according to the preferred features, and obtain a prediction error of each of the prediction models. Then, the processor 130 may select one of the prediction models as a final mental index prediction model according to the prediction error of each of the prediction models. In some embodiments, the prediction models may include a first prediction model, a second prediction model, and an integrated prediction model. A prediction result of the integrated prediction model is a weighted sum of a prediction result of the first prediction model and a prediction result of the second prediction model.

With reference to FIG. 4, in this embodiment, in step S407, the processor 130 may establish a first prediction model according to a first machine learning algorithm and the preferred features. For example, the processor 130 may establish the first prediction model according to the conventional statistical learning algorithms, such as MARS algorithm, LASSO algorithm, or Levenberg-Marquardt (LM) algorithm.

In step S408, the processor 130 may establish a second prediction model according to a second machine learning algorithm and the preferred features. For example, the processor 130 may establish the second prediction model according to a support-vector regression (SVR) algorithm.

In step S409, the processor 130 may establish a third prediction model according to a third machine learning algorithm and the preferred features. For example, the processor 130 may establish the third prediction model according to a deep neural network algorithm.

In step S410, the processor 130 establishes a fourth prediction model according to a fourth machine learning algorithm and the preferred features. Herein, the fourth prediction model may be the integrated prediction model, and a prediction result of the fourth prediction model is a weighted sum of the prediction result of the first prediction model, the prediction result of the second prediction model, and a prediction result of the third prediction model.

In an establishment phase (training phase) of the first/second/third/fourth prediction models, the processor 130 may calculate a prediction error between outputs of the model and the real information according to the real information (e.g., the real NPI score). The prediction error is, for example, a mean absolute percent error (MAPE). Accordingly, in step S411, the processor 130 selects one of the prediction models as the mental index prediction model according to the prediction error of each of the prediction models. Among the first/second/third/fourth prediction models, the processor 130 may select the one with the smallest prediction error as the mental index prediction model.

In summary of the foregoing, in the embodiment of the disclosure, the emotion tags of the subject person in the images are generated based on the facial expression information of the subject person, and the integrated emotion tags in the predetermined time periods are obtained. The mental index prediction model adapted for predicting the mental index may be established through taking the integrated emotion tags as the training data set. That is, this mental index prediction model predicts the mental index of the subject person according to the daily emotional expression of the subject person over successive days. Therefore, in the embodiment of the disclosure, the predicted mental index is generated according to the long-term continuous observation of the subject person, which is of considerable reliability, facilitating diagnosis of psychiatric illnesses, so as to prevent that the subject person is unwilling to express the illness condition, which delays diagnosis of psychiatric illnesses. Besides, the preferred features adapted for establishing the mental index prediction model is determined through the feature extraction, thus increasing the credibility of the model and reducing the calculations. Moreover, taking the sleep quality index and the activity level index estimated based on the images or another instrument as the input features for establishing the mental index prediction model also facilitating prediction of the future emotional development of the subject person, effectively facilitating diagnosis of psychiatric illnesses.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for mental index prediction, adapted for a system for mental index prediction comprising a processor, wherein the method comprises:
    obtaining a plurality of images of a subject person;
    analyzing a plurality of emotion tags of the subject person in the images;
    calculating a plurality of integrated emotion tags in a plurality of predetermined time periods according to the emotion tags respectively corresponding to the images;
    determining a plurality of preferred features according to the integrated emotion tags; and
    establishing a mental index prediction model according to the preferred features to predict a mental index according to the mental index prediction model.

2. The method for mental index prediction according to claim 1, wherein the step of analyzing the emotion tags of the subject person in the images comprises:
    detecting a plurality of facial image blocks of the subject person in the images; and
    inputting the facial image blocks into a facial expression categorization model to obtain the emotion tags respectively corresponding to the images.

3. The method for mental index prediction according to claim 1, wherein the step of calculating the plurality of integrated emotion tags in the plurality of predetermined time periods according to the emotion tags respectively corresponding to the images comprises:
    performing a statistical calculation on the emotion tags in each of the predetermined time periods, and obtaining one of the integrated emotion tags in each of the predetermined time periods.

4. The method for mental index prediction according to claim 1, wherein the step of determining the preferred features according to the integrated emotion tags comprises:
    obtaining a part or all of a plurality of initial features according to the integrated emotion tags; and
    performing feature extraction on the initial features to extract the preferred features.

5. The method for mental index prediction according to claim 4, wherein the step of obtaining a part or all of the initial features according to the integrated emotion tags comprises:
    configuring the integrated emotion tags as a part or all of the initial features.

6. The method for mental index prediction according to claim 4, wherein the step of obtaining a part or all of the initial features according to the integrated emotion tags comprises:
    performing at least one statistical calculation process on the integrated emotion tags to obtain a part or all of the initial features.

7. The method for mental index prediction according to claim 4, further comprising:
    obtaining at least one activity level index of the subject person according to the images; and
    configuring the at least one activity level index as another part of the initial features.

8. The method for mental index prediction according to claim 4, further comprising:
    obtaining at least one sleep quality index of the subject person according to the images or another instrument; and
    configuring the at least one sleep quality index as another part of the initial features.

9. The method for mental index prediction according to claim 1, wherein the step of establishing the mental index prediction model according to the preferred features comprises:
    establishing a plurality of prediction models according to the preferred features, and obtaining a prediction error of each of the prediction models; and
    selecting one of the prediction models as the mental index prediction model according to the prediction error of each of the prediction models.

10. The method for mental index prediction according to claim 9, wherein the prediction models comprise a first prediction model, a second prediction model, and an integrated prediction model, and a prediction result of the integrated prediction model is a weighted sum of a prediction result of the first prediction model and a prediction result of the second prediction model.

11. A system for mental index prediction, comprising:
    a storage device recording a plurality of commands; and
    a processor coupled to the storage device, and configured to execute the commands to:
        obtain a plurality of images of a subject person;
        analyze a plurality of emotion tags of the subject person in the images;
        calculate a plurality of integrated emotion tags in a plurality of predetermined time periods according to the emotion tags respectively corresponding to the images;
        determine a plurality of preferred features according to the integrated emotion tags; and
        establish a mental index prediction model according to the preferred features to predict a mental index according to the mental index prediction model.

12. The system for mental index prediction according to claim 11, wherein the processor is further configured to:
    detect a plurality of facial image blocks of the subject person in the images; and
    input the facial image blocks into a facial expression categorization model to obtain the emotion tags respectively corresponding to the images.

13. The system for mental index prediction according to claim 11, wherein the processor is further configured to:
    perform a statistical calculation on the emotion tags in each of the predetermined time periods, and obtain one of the integrated emotion tags in each of the predetermined time periods.

14. The system for mental index prediction according to claim 11, wherein the processor is further configured to:
    obtain a part or all of a plurality of initial features according to the integrated emotion tags; and
    perform feature extraction on the initial features to extract the preferred features.

15. The system for mental index prediction according to claim 14, wherein the processor is further configured to:
    configure the integrated emotion tags as a part or all of the initial features.

16. The system for mental index prediction according to claim 14, wherein the processor is further configured to:
    perform at least one statistical calculation process on the integrated emotion tags to obtain a part or all of the initial features.

17. The system for mental index prediction according to claim 14, wherein the processor is further configured to:
  obtain at least one activity level index of the subject person according to the images; and
  configure the at least one activity level index as another part of the initial features.

18. The system for mental index prediction according to claim 14, wherein the processor is further configured to:
  obtain at least one sleep quality index of the subject person according to the images or another instrument; and
  configure the at least one sleep quality index as another part of the initial features.

19. The system for mental index prediction according to claim 11, wherein the processor is further configured to:
  establish a plurality of prediction models according to the preferred features, and obtain a prediction error of each of the prediction models; and
  select one of the prediction models as the mental index prediction model according to the prediction error of each of the prediction models.

20. The system for mental index prediction according to claim 19, wherein the prediction models comprise a first prediction model, a second prediction model, and an integrated prediction model, and a prediction result of the integrated prediction model is a weighted sum of a prediction result of the first prediction model and a prediction result of the second prediction model.

\* \* \* \* \*